United States Patent [19]

Goodman et al.

[11] 4,337,207
[45] Jun. 29, 1982

[54] BIOLOGICALLY ACTIVE CATECHOLAMINE DERIVATIVES

[75] Inventors: Murray Goodman, La Jolla; Michael S. Verlander, Del Mar; Kenneth A. Jacobson, La Jolla; Kenneth L. Melmon, Woodside; Neal Castagnoli, San Rafael, all of Calif.

[73] Assignee: Regents of the University of California, Berkeley, Calif.

[21] Appl. No.: 184,000

[22] Filed: Sep. 4, 1980

[51] Int. Cl.$^3$ ............................................. C07C 103/29
[52] U.S. Cl. ................................. 260/404.5; 260/404; 562/444; 564/165; 424/309; 424/324
[58] Field of Search .......................... 564/165; 562/444; 260/404, 404.5 R

[56] References Cited

U.S. PATENT DOCUMENTS 3,732,300  5/1973  Lunts et al. ........................ 564/165
4,146,638  3/1979  Renth et al. ........................ 564/165

FOREIGN PATENT DOCUMENTS 927896   6/1963  United Kingdom .
1360457  7/1974  United Kingdom .

OTHER PUBLICATIONS

Wagner et al., Synthetic Organic Chemistry, John Wiley & Sons, N.Y., N.Y., 1955, pp. 660–661.

Primary Examiner—Arthur P. Demers
Attorney, Agent, or Firm—Phillips, Moore, Lempio & Majestic

[57] ABSTRACT

Biologically active derivatives of norepinephrine are disclosed. Such derivatives are catecholamines wherein isoproterenol is modified by extending the isopropyl functional grouping to an alkyl, aryl, or alkyl-aryl chain of variable length where said chain terminates in a carboxylic acid functional group, or in a substituted amide functional group. Such derivatives are β-adrenergic and a number of such derivatives e.g., 6-(β-3,4-dihydroxyphenyl-β-hydroxy)-ethylamino heptanoic acid p-toluide, 6-(β-3,4-dihydroxyphenyl-β-hydroxy)-ethylamino heptanoic acid para-n-butyl anilide; 6-(β,3,4-dihydroxyphenyl-β-hydroxy)-ethylamino heptanoic acid para-methoxy anilide; 6-(β-3,4-dihydroxyphenyl-β-hydroxy)-ethylamino heptanoic acid paratrifluoromethyl anilide; and 6-(β-3,4-dihydroxyphenyl-β-hydroxy)-ethylamino heptanoic acid N-methyl para-toluide display a β-adrenergic activity at least several orders of magnitude greater than isoproterenol itself. Several methods of producing such active derivatives are also disclosed.

29 Claims, No Drawings

BIOLOGICALLY ACTIVE CATECHOLAMINE DERIVATIVES

DESCRIPTION

BACKGROUND OF THE INVENTION

The role of the hormone norepinephrine, 4-(2-amino-1-hydroxyethyl)-1,2-benzenediol, and its congeners such as epinephrine or isoproterenol as transmitter substances of the peripheral sympathetic nerve endings and of certain synapses in the central nervous system is well documented. Epinephrine, 4-[1-hydroxy-2-(methyamino)-ethyl]-1,2-benzenediol, which acts as a stimulator of the sympathetic nervous system, thus producing a broad range of physiological effects such as vasopression, increased blood pressure, cardiac stimulation, increased cardiac output, glucose release and glycogenolysis, is also extremely well known and studied. Generically in a chemical sense, such hormones are classified as catecholamines. That is, they possess the characteristic hydroxyl groups substituted at the 3 and 4 positions on a benzene ring and the hydroxy-alkylamine side chain attached to the number 1 carbon of the benzene ring. More specifically norepinephrine has the structure:

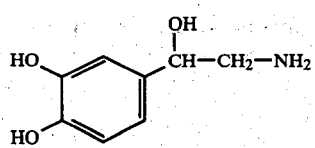

while epinephrine has the structure:

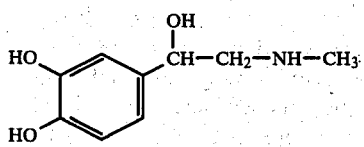

Although norepinephrine and epinephrine are closely related chemically, their physiological effects are somewhat different with respect to reactions mediated by the hormones, tissue and organs affected, and the strength of their respective activities. Thus, norepinephrine primarily mediates nerve impulses as a transmitter substance of the sympathetic nerve endings. Epinephrine, on the other hand, operates primarily as a vasopressor, heart stimulant, and blood volume and pressure stimulant. The two molecular structures norepinephrine and epinephrine produce qualitatively similar but quantitatively different physiological effects. In some instances these effects are diverse and general, whereas, in others, the effect is very specific. It is therefore of interest to explore the possibility of devising epinephrine and norepinephrine related molecules which will exhibit biological activity in general and perhaps selected activity which will permit "targeting" various physiological functions on a more selective basis than is possible with the naturally occurring hormones.

Unfortunately, the epinephrine and norepinephrine structures, (generically-catecholamines) are particularly sensitive to alteration of the molecular structure insofar as maintenance of physiological activity is concerned. Thus when aromatic substitutions are made at the 2 or 5 carbon positions on the benzene ring, activity may be destroyed. On the other hand, a number of active molecules have been obtained by alkylation of the side chain amine group, e.g., the isopropyl homolog of epinephrine, isoproterenol; which has the structure:

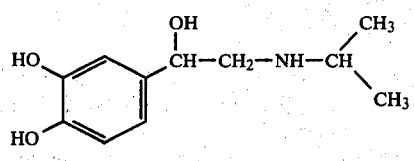

The preparation of other biologically active catecholamines would, of course, be of great interest, especially where such derivatives may exhibit specialized effects on biological systems, or where the derivative could be further conjugated with other "carrier" molecular structures without affecting the basic physiological functions which are characteristic of the catecholamine hormones.

BRIEF SUMMARY OF THE INVENTION

The present invention is directed to modified catecholamine hormones wherein isoproterenol is chemically modified by extending the side chain isopropyl group to add further an alkyl or alkyl-aryl chain of variable length to terminate in a carboxylic acid group or carboxylic acid derivatives such as an amide or substituted amide. Such modified catecholamine hormones have the general structure:

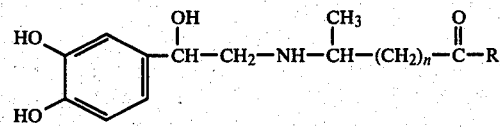

In order to prevent self-degradation upon storage, the modified catecholamines are usually prepared in the protonated form, i.e.:

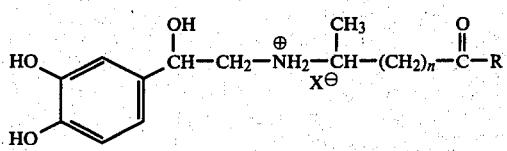

wherein $X^\ominus$ may be any pharmaceutically acceptable anion such as chloride, acetate, sulfate, phosphate and the like.

It is an object of the invention to provide biologically active derivatives of norepinephrine or isoproterenol.

It is another object of the invention to provide isoproterenol derivatives which exhibit $\beta$-adrenergic activity.

It is still another object of the invention to provide $\beta$-adrenergically active derivatives of isoproterenol wherein the catecholamine is modified by extending the isopropyl group to an alkyl chain of variable length and terminating in a carboxylic acid group or a substituted amide group.

It is a further object of the invention to prepare $\beta$-adrenergically active derivatives of isoproterenol having the general formula:

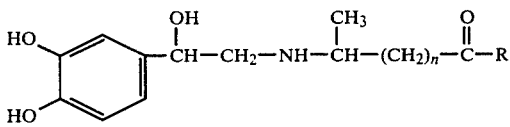

wherein n is 1 to 15 and —CO—R is a carboxylic acid group or a carboxylic acid derivative such as an amide or substituted amide.

Other objects and advantages of the invention will be apparent from the following description and the appended claims.

DETAILED DESCRIPTION OF THE INVENTION

The present invention relates to derivatives of isoproterenol which exhibit biological activity; and more specifically to isoproterenol derivatives wherein isoproterenol is modified by the addition of alkyl or alkyl-aryl chains of variable length to the side chain amino functional group. Such added chains are further characterized by their termination in a carboxyl functional group or in a derivative of a carboxylic acid such as an amide in a substituted amide.

Generically, the biologically active isoproterenol derivatives have the structure:

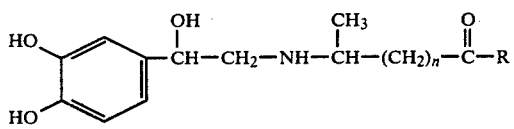

wherein n indicates the number of methylene groups in the chain, but which is most usually from 1 to perhaps 15, and R may be either —OH, i.e., a carboxylic acid termination; or —NH—R', i.e., an amide termination.

While it is indicated that the added alkyl chain is a straight chain, it should be understood that the chain may also be branched; and may even include aryl groupings or mixed alkyl-aryl groupings. The important criterion is the retention or enhancement of β-adrenergic activity. In any event, however, the straight chain alkyls i.e., —(CH$_2$)$_n$— do appear to favor the retention of the β-adrenergic activity.

It is of equal importance that the added N substituent grouping terminates in a carboxyl functional group, i.e., —COOH; or in an amide, i.e., —CO—NH—R' generally where R' can be H (a primary amide) or a variety of alkyl or aryl groups as outlined below. Such terminal amides may be derived from aromatic amines such as aniline and aniline derivatives such as para-toluidine,

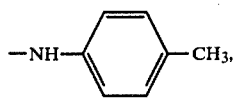

which is especially preferred; para-n-butyl aniline,

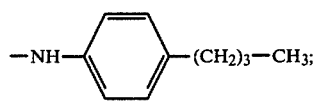

p-methoxy aniline,

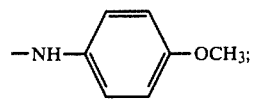

p-trifluoromethyl aniline,

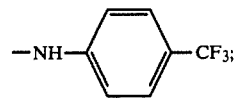

n-methyl p-toluidine,

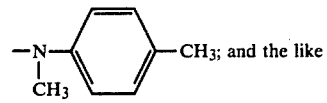

and the like

The terminal amide group may also be derived from alkyl amines, e.g., n-butyl amine

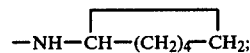

or similar straight or branch chain amines or cycloalkyl amines e.g., cyclohexyl amine,

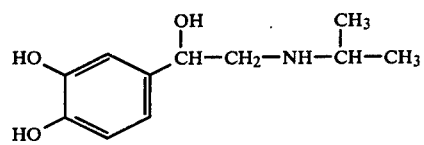

or the like.

As noted previously, inspection of the structure of the biologically active norepinephrine derivatives will reveal that there is a side-chain methyl group attached to the carbon immediately adjacent the side chain amine. Since isoproterenol has the structure:

it will be apparent that the compounds of the invention may also be characterized as isoproterenol derivatives. That is, the invention compounds may be characterized as modifications of isoproterenol wherein the terminal isopropyl group is extended to an alkyl chain, or alkyl-aryl chain of variable length wherein the chain terminates in a carboxylic acid or substituted amide.

Such modified and extended isoproterenol derivatives have demonstrated β-adrenergic activity in vitro by measuring cyclic AMP (cAMP) formation in S49 mouse lymphoma cells, and in vivo activity by monitoring changes in the blood pressure and heart rate of rats. The in vitro testing of cAMP formation in S49 lymphoma cells is a well documented and accepted test for indicating and anticipating β-adrenergic activity in the mammalian body.

Although the general structure of the invention derivatives was noted above in the "amine" form, i.e.,

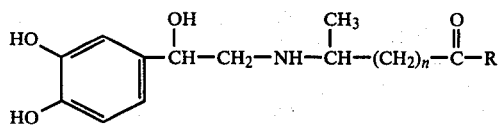

from a practical standpoint, the compounds are normally prepared in the protonated form, i.e.,:

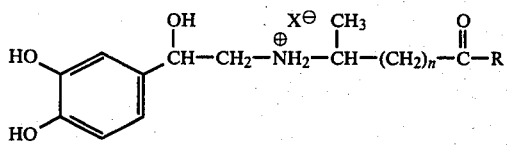

wherein $X^\ominus$ may be any pharmaceutically acceptable anion such as acetate, chloride, sulfate, phosphate etc. The protonated salt form of the derivative exhibits far greater stability in storage than the "amine" form which undergoes internal degradation reactions, thus destroying its activity.

Methods for Synthesizing the Derivatives

The carboxylic acid terminated isoproterenol derivatives may be synthesized by a reductive amination reaction between norepinephrine and the appropriate ketoacid. The reductions are performed in the presence of platinum oxide (PtO$_2$) catalyst at room temperature and at atmospheric pressure under hydrogen. The reaction is carried out in methanol or in mixtures of methanol and acetic acid.

The reaction scheme (Route A) is:

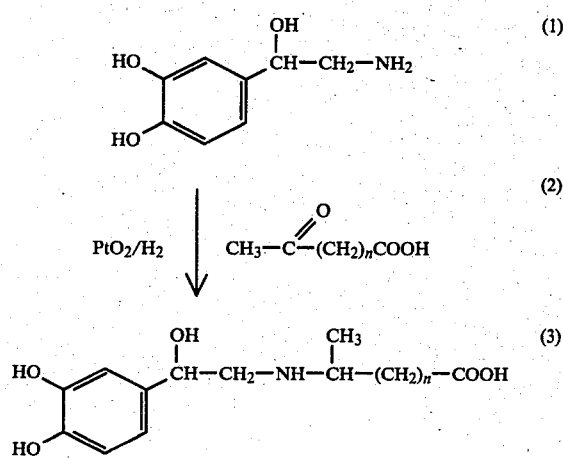

The substituted amide terminated norepinephrine derivatives may be synthesized in some instances, by carbodiimide coupling of the carboxylic acid terminated derivative. The carbodiimide coupling agent may be water soluble, such as 1-ethyl-3(3 dimethyl-aminopropyl)carbodiimide hydrochloride; or water insoluble, such as dicyclohexyl carbodiimide, depending on the solubility of the amine to which the carboxylic acid is being coupled. Thus a carboxylic acid terminated derivative as prepared in the reaction scheme noted above, may, in turn, be converted into the substituted amide by reacting the carboxylic acid derivative with the desired substituted amine in the presence of carbodiimide.

The reaction scheme is (Route A):

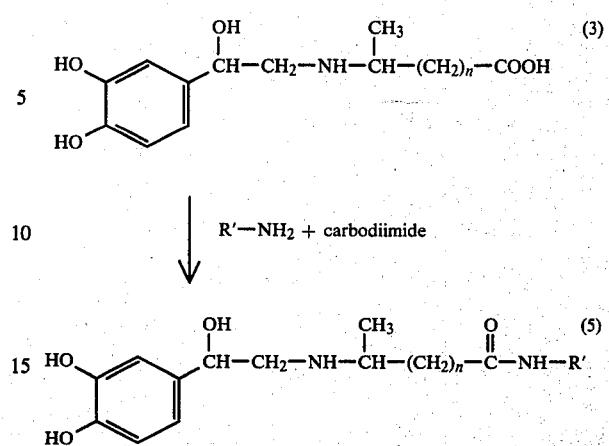

The carbodiimide reaction path is generally suitable only for chain lengths where n=4 or higher. Shorter members of the series tend to form lactams under the coupling conditions.

Therefore, a more general synthesis scheme (Route B) for the production of the substituted amide derivatives is the reductive amination of the appropriate ketoamide with norepinephrine.

The appropriate ketoamide may be prepared from the keto acid by reaction with the appropriate amine and a coupling agent such as a carbodiimide. The keto acids, in turn, can be previously prepared in accordance with methods well known in the prior art.

The general synthesis of the amides via Route B is:

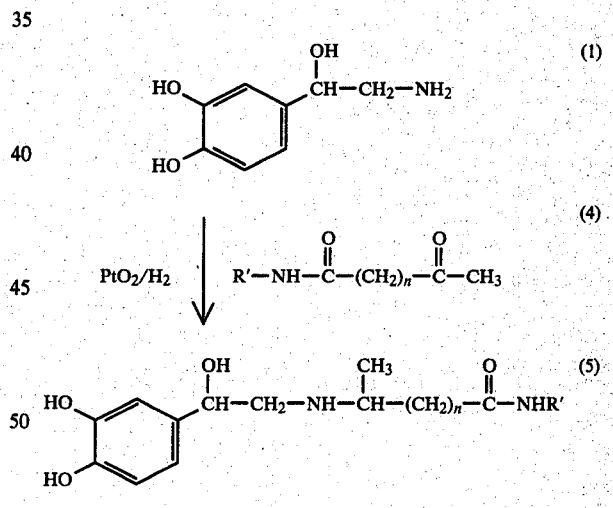

Synthesis of Representative Compounds

All of the catecholamine derivatives can be synthesized by one of several general routes as noted above. For clearer understanding specific examples are described below. From a review of these examples, the synthesis of all the relevant catecholamines will be apparent.

Synthesis of 6-($\beta$-3,4-Dihydroxyphenyl-$\beta$-hydroxy)-ethylamino heptanoic acid p-Toluide This target molecule was prepared by the two routes A and B, outlined above.

Route A

δ-Acetyl-n-valeric Acid (see Compound (2) in Route A above where n=4)

This compound was prepared from 2-methylcyclohexanol according to Schaeffer and Snoddy (Org. Syn., 31, 3 (1951)).

6-(β-3,4-Dihydroxyphenyl-β-hydroxy)-ethylamino heptanoic acid (see Compound (3) above where n=4 and, Table 1, Compound 6)

Norepinephrine as the free base (see compound 1 above, 3.91 g, 0.023 mmol) and δ-acetyl-n-valeric acid (see Compound (2) above where n=4, 7.50 g, 0.046 mmol) were dissolved in 20% acetic acid mixed into methanol (75 ml). Hydrogenation was performed overnight at room temperature and atmospheric pressure over 0.1 g $PtO_2$ catalyst. After filtration and washing with acetic acid until only platinum black remained on the filter, the combined filtrate was evaporated. The resulting thick oil was dissolved in methanol and gradually added to ethyl ether. The whitish precipitate was filtered, washed with ether, and dried in vacuo giving 5.06 g of an amorphous solid (compound 6, Table 1, 74% yield), which was homogeneous by TLC and NMR.

The following compound was prepared by two methods using different carbodiimide coupling agents:

6-(β-3,4-dihydroxyphenyl-β-hydroxy)-ethylamino Heptanoic Acid p-Toluide (Compound 12 in Table 1 below)

Method(i)

p-Toluidine hydrochloride was prepared by addition of 4 N HCL/dioxane to a solution of the free base in ether. The crystals were collected by filtration, washed with ether, and dried in vacuo.

Compound (3), n=4 (2.97 g, 10 mmol), i.e., and p-toluidine hydrochloride (1.86 g, 13 mmol) were added to 0.05 M monosodium phosphate (400 ml) under an inert atmosphere. 1-Ethyl-3(3-dimethyl-aminopropyl)-carbodiimide HCl (Sigma, 3.3 g, 17 mmol) was added. After one day the solution was extracted with chloroform (four times) and with n-butanol (three times). The combined butanol extracts were evaporated under reduced pressure at 40° C. The resulting oil was redissolved in butanol, filtered, and evaporated without delay. This oil was transformed into a white amorphous solid by stirring under ether. The solid was filtered, washed with ether, and dried in vacuo giving 1.73 g (41% yield) of the hydrochloride salt of the title compound (Compound 12, Table 1).

Method (ii)

Compound (3) above, (n=4,102 mg, 2 equivalents) and p-toluidine hydrochloride (25 mg, 1 equivalent) were dissolved in 5 ml of pyridine/water (80%, v/v). Dicyclohexylcarbodiimide (88 mg, 2.5 equivalents) was added and the solution was stirred under nitrogen overnight. Solvent was removed under reduced pressure at 40° C. until a white precipitate formed. Water (15 ml) was added and the urea was removed by filtration through Celite.

The solution was passed over a bed of Bio-Rex 70 cation exchange resin (Bio-Rad, 2 g dry weight) in the H+ form. After washing the bed thoroughly with $H_2O$, the product was removed from the resin with 5% acetic acid. After lyophilization, there remained 40 mg (51% yield) of a white solid, the acetate salt of the title compound (Compound 12, Table 1, $X=CH_3COO$). This was shown by TLC to be identical to the product prepared by method (i) and free from starting materials.

Route B

δ-Acetyl-n-valeric Acid p-Toluide (see Compound (4) above where n=4)

δ-Acetyl-n-valeric acid (1.2 g) and p-toluidine (1.0 g) were dissolved in tetrahydrofuran (30 ml). Dicyclohexylcarbodiimide was added and the solution stirred overnight. The solvent was removed, and the residue suspended in ethyl acetate and filtered. After washing with 0.1 N hydrochloric acid, saturated sodium bicarbonate, and water, the organic layer was dried over magnesium sulfate. The solution was filtered and evaporated. Recrystallization of the residue from ethyl acetate/hexane gave 1.36 g (70% yield) of white crystals. The δ-acetyl-n-valeric acid p-toluide (see Compound (4) above) so produced had a m.p. of 106°–107.5° C. Analysis calculated for $C_{14}H_{19}NO_2$: C, 72.07; H, 8.21; N, 6.00. Found: C, 71.86; H, 8.28; N, 6.04.

Norepinephrine, free base (1, 30 mg, 0.16 mmol) and Compound (4) above (n=4, 74.5 mg, 0.32 mmol) were dissolved in acetic acid (1 ml). $PtO_2$ catalyst (10 mg) was added and the mixture was hydrogenated at atmospheric pressure overnight. The solution was removed from the catalyst and added to 0.01 N hydrochloric acid, after which extractions with ethyl acetate and n-butanol were performed. The combined butanol extracts were evaporated, redissolved in n-butanol, filtered through a glass wool plug in a Pasteur pipette, and evaporated. The oil was dried in vacuo giving 62 mg of the HCl salt of the title compound (Compound 12, Table 1, X=Cl).

Biological Activity

The following Table 1 sets forth the results of the testing of biological activity of the indicated norephinephrine derivatives.

The activities, i.e., $K_A$ and $E_{max}$, were observed in tests of the noted catecholamines on S49 lymphoma cells, which is utilized as a measure of agonist activity. Such testing procedures and their significance has been set forth in a number of prior publications, e.g. Shear et al., J. Biol. Chem.; 251, 7572 (1976); Coffino, et al., In Vitro, 14, No. 1, 140 et.seq. (1978); and in Johnson, et al.; Molecular Pharmacology, 15, 16–27 (1978). The tests measure increased cyclic adenosine monophosphate (cAMP) concentration in the S49 cells. In Table 1, $K_A$ indicates the concentration of the catecholamine for approximately half maximal stimulation of cAMP concentration. $E_{max}$ is a measure of the maximal response (cAMP concentration) of the S49 cells to the respective catecholamines regardless of how high the concentration of the catecholamines may become. The Table compares the response of the cells to the particular catecholamine derivatives with the cells' response to isoproterenol. Thus a measure of the relative biological activity can be obtained.

TABLE 1
Biological Activity of Catecholamine Derivatives

Structure:

HO-[benzene ring]-CH(OH)-CH$_2$-NH$_2^{\oplus}$(X$^{\ominus}$)-CH(CH$_3$)-(CH$_2$)$_n$-C(=O)-R with HO at two positions on the ring.

| Compound | R | n | Synthesis[a] | $K_A$ (M) | $E_{max}$ | d,l-Isoproterenol $K_A$ (M) | $E_{max}$ |
|---|---|---|---|---|---|---|---|
| 6 | —OH | 2 | Route B | $0.16 \times 10^{-5}$ | 273 | $0.25 \times 10^{-9}$ | 366 |
| 7 | —OH | 3 | Route B | $0.37 \times 10^{-6}$ | 254 | $0.25 \times 10^{-9}$ | 366 |
| 8 | —OH | 4 | Route B | $0.35 \times 10^{-6}$ | 282 | $0.34 \times 10^{-9}$ | 414 |
| 9 | —OH | 5 | Route B | $0.35 \times 10^{-6}$ | 170 | $0.29 \times 10^{-9}$ | 248 |
| 10 | —NH—C$_6$H$_4$—CH$_3$ | 2 | Route B | $0.35 \times 10^{-8}$ | 147 | $0.25 \times 10^{-8}$ | 186 |
| 11 | —NH—C$_6$H$_4$—CH$_3$ | 3 | Route B | $0.80 \times 10^{-8}$ | 171 | $0.25 \times 10^{-8}$ | 186 |
| 12 | —NH—C$_6$H$_4$—CH$_3$ | 4 | Routes A, B | $0.56 \times 10^{-10}$ | 201 | $0.25 \times 10^{-8}$ | 186 |
| 13[b] | —NH—C$_6$H$_4$—CH$_3$ | 4 | Route B | $0.60 \times 10^{-11}$ | 269 | $0.43 \times 10^{-10}$ | 341 |
| 14 | —NH—C$_6$H$_4$—CH$_3$ | 5 | Route A | $0.22 \times 10^{-7}$ | 195 | $0.25 \times 10^{-8}$ | 186 |
| 15 | —NH—C$_6$H$_4$—(CH$_2$)$_3$CH$_3$ | 4 | Route B | $0.59 \times 10^{-15}$ | 151 | $0.77 \times 10^{-12}$ | 124 |
| 16 | —NH—C$_6$H$_4$—OCH$_3$ | 4 | Route B | $0.13 \times 10^{-7}$ | 166 | $0.40 \times 10^{-7}$ | 136 |
| 17 | —NH—C$_6$H$_4$—CF$_3$ | 4 | Route B | $< 10^{-15}$ | 150 | $0.77 \times 10^{-12}$ | 124 |
| 18 | —N(CH$_3$)—C$_6$H$_4$—CH$_3$ | 4 | Route B | $0.22 \times 10^{-13}$ | 206 | $0.16 \times 10^{-11}$ | 192 |
| 19 | —NH—(CH$_2$)$_3$—CH$_3$ | 4 | Routes A, B | $0.18 \times 10^{-9}$ | 229 | $0.45 \times 10^{-10}$ | 318 |
| 20 | cyclic CH—(CH$_2$)$_4$—CH$_2$—NH | 4 | Routes A, B | $0.26 \times 10^{-9}$ | 245 | $0.45 \times 10^{-10}$ | 318 |

[a]Refer to description
[b]from L-norepinephrine

A large dependence of activity on the length of the methylene chain i.e., (CH$_2$)$_n$ is seen with the toluides (Compounds 10–14). Of the compounds noted, peak activity is seen in the case of n=4 (Compound 12), which has an activity approximately two orders of magnitude greater than that of isoproterenol. These results are supported by data from rat testing, which have shown that Compound 12 is 50–70 times more active than isoproterenol, when blood pressure and heart rate changes are monitored on administration of the drug. Furthermore, the $K_D$'s for compound 12 (the concentration of drug at which half the receptors are not occupied) in S49 and C6 cells are 2 orders of magnitude lower than would be found for isoproterenol.

Similarly, there is a dependence on the nature of the substituent group on the amide, aromatic amides (Compounds 10–18) being considerably more biologically active than aliphatic amides (Compounds 19–20) in this test. The nature of substituent groups on the ring of aromatic amides also appears to exert a profound effect on biological activity in these compounds. Thus Compound 16, for example, which contains a methoxyl group on the ring has approximately the same activity as isoproterenol in the S49 cell assay. Compound 12, on the other hand, which has a methyl group at the para position on the ring is almost 2 orders of magnitude more active than isoproterenol; and Compounds 15 and 17 which contain n-butyl and trifluoromethyl substituents, respectively, are at least 3 orders of magnitude more active than isoproterenol. Thus it can be expected that elaboration of the substituent groups on the aromatic ring will lead to a wide variety of β-adrenergic drugs.

We claim:

1. β-adrenergic compounds having the formula:

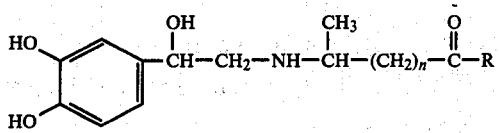

wherein n=1 to 15, and R is NHR', where R' is H or an alkyl, aryl, or alkyl-aryl substituent.

2. β-adrenergic compounds in the protonated form:

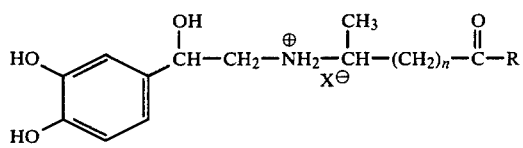

wherein n=1 to 15, R is NHR′, where R′ is an H or alkyl, aryl, or alkyl-aryl substituent and X⊖ is a pharmaceutically acceptable anion.

3. The compounds of claim 1 wherein n=1 to 5.
4. The compounds of claim 1 wherein n=4.
5. β-adrenergic compounds having the formula:

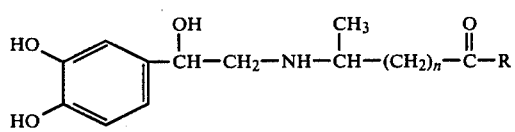

wherein n=1 to 15, and R is an aniline derivative.

6. The compounds of claim 5 wherein n=4.
7. The compounds of claim 5 wherein the aniline derivative is

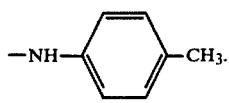

8. The compounds of claim 7 wherein n=4.
9. The compounds of claim 5 wherein the aniline derivative is

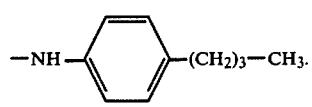

10. The compounds of claim 9 wherein n=4.
11. The compounds of claim 5 wherein the aniline derivative is

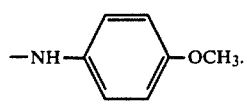

12. The compounds of claim 11 wherein n=4.
13. The compounds of claim 5 wherein the aniline derivative is

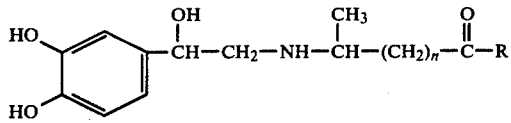

14. The compounds of claim 13 wherein n=4.
15. The compounds of claim 5 wherein the aniline derivative is:

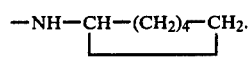

16. The compounds of claim 15 wherein n=4.
17. β-adrenergic compounds having the formula:

HO—⟨benzene(HO)⟩—CH(OH)—CH₂—NH—CH(CH₃)—(CH₂)ₙ—C(=O)—R wherein n=1 to 15, and R is an alkyl amine.
18. The compounds of claim 17 wherein n=4.
19. The compounds of claim 17 wherein the alkyl amine is —NH(CH₂)₃—CH₃.
20. The compounds of claim 19 wherein n=4.
21. β-adrenergic compounds having the formula:

HO—⟨benzene(HO)⟩—CH(OH)—CH₂—NH—CH(CH₃)—(CH₂)ₙ—C(=O)—R wherein n=1 to 15, and R is a cyclo alkyl amine.
22. The compounds of claim 21 wherein n=4.
23. The compounds of claim 21 wherein the cyclo alkyl amine is

—NH—CH—(CH₂)₄—CH₂.
   └─────────────┘

24. The compounds of claim 23 wherein n=4.
25. The compound 6-(β-3,4-dihydroxy phenyl-β-hydroxy)-ethylamino heptanoic acid p-toluide and pharmaceutically acceptable salts thereof.
26. The compound 6-(β-3,4-dihydroxy phenyl-β-hydroxy)-ethylamino heptanoic acid para-n-butyl anilide and pharmaceutically acceptable salts thereof.
27. The compound 6-(β-3,4-dihydroxy phenyl-β-hydroxy)-ethylamino heptanoic acid para-methoxy anilide and pharmaceutically acceptable salts thereof.
28. The compound 6-(β-3,4 dihydroxy phenyl-β-hydroxy)-ethylamino heptanoic acid para-trifluoromethyl anilide and pharmaceutically acceptable salts thereof.
29. The compound 6-(β-3,4-dihydroxy phenyl-β-hydroxy)-ethylamino heptanoic acid N-methyl para-toluide and pharmaceutically acceptable salts thereof.

* * * * *